United States Patent [19]

Karger et al.

[11] Patent Number: 5,322,608
[45] Date of Patent: Jun. 21, 1994

[54] SILOXANDEDIOL COATING FOR CAPILLARY ELECTROPHORESIS AND FOR GENERAL SURFACE MODIFICATION

[75] Inventors: Barry L. Karger, Newton; Dieter Schmalzing, Boston; Frantisek Foret, Malden, all of Mass.

[73] Assignee: Northeastern University, Boston, Mass.

[21] Appl. No.: 994,832

[22] Filed: Dec. 23, 1992

[51] Int. Cl.$^5$ .............................................. C25B 9/00
[52] U.S. Cl. ................................................ 204/299 R
[58] Field of Search .................................. 204/299 R

[56] References Cited

U.S. PATENT DOCUMENTS

| | | | |
|---|---|---|---|
| 2,490,357 | 12/1949 | Hyde | 260/46.5 |
| 3,214,420 | 10/1965 | Hunt | 260/89.7 |
| 4,680,201 | 7/1987 | Hjerten | 427/230 |
| 4,690,749 | 9/1987 | Van Alstine et al. | 204/299 R |
| 4,931,328 | 6/1990 | Swedberg | 428/36.91 |
| 5,074,982 | 12/1991 | Novotny et al. | 204/182.8 |
| 5,082,559 | 1/1992 | Eguchi et al. | 210/198.2 |
| 5,110,439 | 5/1992 | Holloway | 204/299 R |
| 5,112,460 | 5/1992 | Karger et al. | 204/182.8 |

OTHER PUBLICATIONS

Dean, "Silicone Adhesive Sealants and Adhesives" in Skeisd, *Handbook of Adhesives*, 3rd ed. 522–535 (1990).
Hjerten, "High Performance Electrophoresis Elimination of Electroendosmosis and Solute Adsorption", J. Chromatography 347:191–198 (1985).
Huang et al., "Evaluation of Surface-bonded Polyethylene Glycol and Polyethylene Imine in Capillary Electrophoresis", J. Microcol. 4:135-143 (1992).

*Primary Examiner*—John Niebling
*Assistant Examiner*—C. Dolacroix-Muirheid
*Attorney, Agent, or Firm*—Weingarten, Schurgin, Gagnebin & Hayes

[57] ABSTRACT

A coated microcapillary column for high performance electrophoresis is disclosed. A preferred microcapillary includes a column; a universal sub-layer of coating material that has been highly crosslinked using a crosslinking agent and attached covalently or non-covalently to the column wall; and a variable top layer of a monomer or polymer, preferably crosslinked, attached to the sub-layer. The microcapillary preferably is prepared by covalently bonding a highly crosslinked siloxanediol sub-layer to the inner surface of the microcapillary wall and then causing a mixture of monomers or polymers to react in the bore of the microcapillary to form a top layer. The bilayer coating as used in a microcapillary prevents adsorption of solutes during electrophoresis and eliminates or controls electroosmotic flow. The disclosed coating may also be formed on other kinds of surfaces where similar surface modification is desired. The sub-layer, which can be formed from other siloxane derivatives having two nucleophilic end groups, e.q., diamino or dithiol, may be used independently, or as a base layer for bilayer or even multilayer surface formation.

10 Claims, 7 Drawing Sheets

SILOXANDEDIOL COATING FOR CAPILLARY ELECTROPHORESIS AND FOR GENERAL SURFACE MODIFICATION

FIELD OF THE INVENTION

This invention relates to coatings for surfaces, and more particularly, to coatings suitable for capillary electrophoresis columns.

BACKGROUND OF THE INVENTION

Capillary electrophoretic separation techniques find wide application in the biologically related sciences. Molecular species such as peptides, proteins, oligonucleotides, and oligosaccharides are separated by causing them to migrate in a buffer solution under the influence of an electric field. The separation is normally carried out in thin-walled, narrow-bore capillary tubes to minimize the evolution of heat during electrophoretic separation, which would cause zone deformation.

Among the other mechanisms that can cause zone deformation are non-uniform electroendosmosis and adsorption to the inner surface of the capillary of the substances to be separated. However, the problems associated with adsorption and non-uniform electroendosmosis can be overcome by coating the inner wall of the electrophoresis tube with various polymeric substances.

In U.S. Pat. No. 4,680,201, Hjerten discloses a method for coating the inner wall of a narrow bore capillary with a monomolecular polymeric coating of polyacrylamide bonded to the capillary wall by means of a bifunctional reagent, e.g., γ-methacryloxypropyltrimethoxysilane. These capillaries can be used for free-zone electrophoresis in open tubes.

Novotny et al., U.S. Pat. No. 5,074,982, discloses that the inner wall of silica capillaries used in electrophoretic separations can be coated with bifunctional reagent using a Grignard reagent, for hydrolytic stability.

Holloway, U.S. Pat. No. 5,110,439, shows a polyacrylamide gel electrophoresis column having a fused silica tube, a polyacrylamide gel matrix, and chains of non-crosslinked polydimethylsiloxane radially between and covalently attached to both the tube and the gel matrix.

Huang et al. (J. Microl. Sepns. 4:135-143, 1992) reports a procedure for bonding polyethylene glycol and polyethylene imine onto the surface of a microcapillary tube. The capillary surface is first treated to create a uniform, dense distribution of silanol groups for bonding of a silicon hydride polymer. At elevated temperature, e.g., 250° C., the Si—H groups in the polymer mixture reacted with the silanol groups on the capillary surface and remaining Si—H groups crosslinked polymer chains. Free-radical reactions through Si—CH$_3$ groups further crosslinked the polymer chains.

SUMMARY OF THE INVENTION

The present invention generally features a coating suitable for surfaces such as are found in capillary electrophoresis columns. The coating includes a universal, highly crosslinked, sub-layer to which a variable top layer or layers may be attached. The sub-layer of the coating of the invention is formed, in general, by attaching to the desired surface a layer of a polymeric coating material comprising a siloxane derivative having two nucleophilic end groups (e.g., siloxanediol) and crosslinking individual polymers of the coating material using a crosslinking agent. The crosslinking step can be performed either before or after the attaching step, and the attachment between the surface and the polymeric coating material can be either covalent or non-covalent. A preferred coating material is polymethylvinylsiloxanediol.

Preferably, the polymeric coating material includes a plurality of non-nucleophilic attachment centers, which may be the site for further covalent or non-covalent attachment of a second layer of the coating. The polymers of the second layer may also be crosslinked. A preferred second layer coating material is polyacrylamide, which may be further crosslinked through the amino groups with formaldehyde.

A preferred microcapillary column of the invention includes a microcapillary having an interior cavity and a wall with an inner surface; a sub-layer of a siloxanediol polymeric coating material highly crosslinked with a crosslinking agent and attached covalently or non-covalently to the inner surface of the wall; and a top layer of crosslinked or non-crosslinked coating material attached covalently or non-covalently to the sub-layer coating material.

The coating of the invention creates a new, stable surface, provides for the stability of the coating over a wide pH range, and allows highly efficient grafting and/or adsorption of a variable top layer or layers, if desired. As used in capillary electrophoresis, the coating suppresses or controls electroosmotic flow and prevents adsorption of analytes to the surface of the column.

Using a crosslinking agent for stabilizing the coating instead of the known method of free radical formation means that the crosslinking reaction can be performed at room temperature. This permits wide latitude in the types and numbers of groups that can be associated with the polymeric coating material as non-nucleophilic attachment centers. At higher temperatures, during free radical crosslinking, many of the preferred groups, e.g., vinyl, epoxy, etc., are destroyed. A much denser second layer can be formed, therefore, when the coating of the invention serves as a sub-layer of a multi-layer construct than is the case with other materials. The chemical reactions for polymerization, crosslinking, and modification of the coating are very easily carried out, permitting a wide variety of properties and uses.

BRIEF DESCRIPTION OF THE DRAWINGS

Other features and advantages of the invention will be apparent from the following description of the preferred embodiments thereof, taken in conjunction with the accompanying drawings, in which.

DETAILED DESCRIPTION OF THE INVENTION

Figure 1:
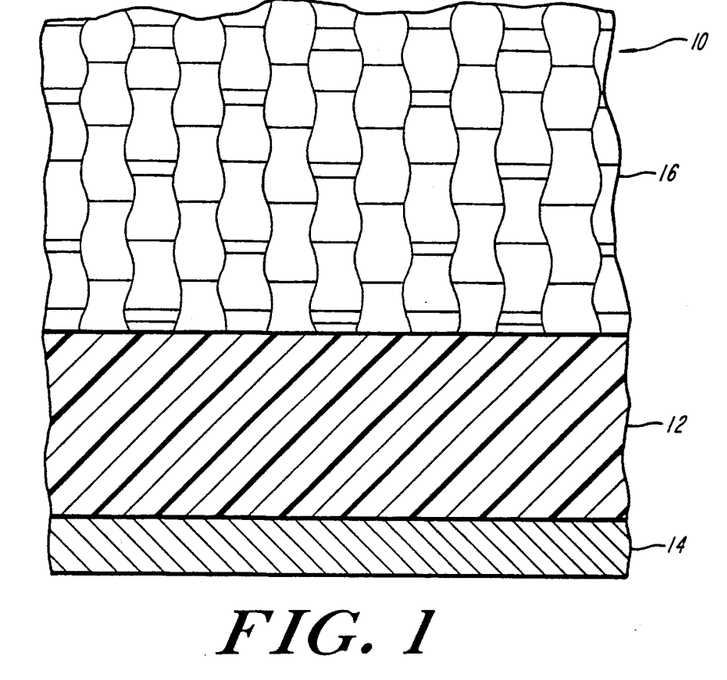
FIG. 1 shows a cross-sectional view of a coated microcapillary column of one embodiment of the invention.

The invention, as applied in capillary electrophoresis, provides for a highly crosslinked coating for the interior of a separation capillary. As shown in FIG. 1, a microcapillary column of the invention includes a microcapillary 10; a sub-layer 12 of a siloxane derivative having two nucleophilic end groups, e.g., siloxanediol, covalently or non-covalently attached to the interior surface 14 of the microcapillary and extensively crosslinked, preferably at room temperature, using a crosslinking agent and not free radical formation; and a top coating layer 16 of any type of molecule that is able to attach (covalently or non-covalently) to the multiple internal non-nucleophilic centers of the crosslinked siloxanediol layer.

The microcapillary may be made of any of a variety of materials provided that the detection system to be employed in the electrophoresis can function adequately with the particular material used. Suitable materials include fused silica, glass, alumina, beryllia, and TEFLON TM. Preferably, the microcapillary is made of fused silica.

The first interior coating layer (sub-layer 12) preferably consists of a highly crosslinked polymethylvinylsiloxanediol covalently attached to the interior surface of the separation column. This siloxanediol base layer provides pH stability for the coating, and through its double bonds, a platform for grafting on or adsorbing a dense final top layer. The top layer 16 preferably consists of a highly crosslinked polymethylolacrylamide grafted to the siloxanediol. The polymethylolacrylamide top layer suppresses or controls electroosmotic flow and prevents the adsorption of the analytes to the surface of the column. In addition, the coating provides stability over a wide pH range and a high degree of experimental reproducibility. The columns can be used over many hundreds of runs in high electric fields.

Figure 2:
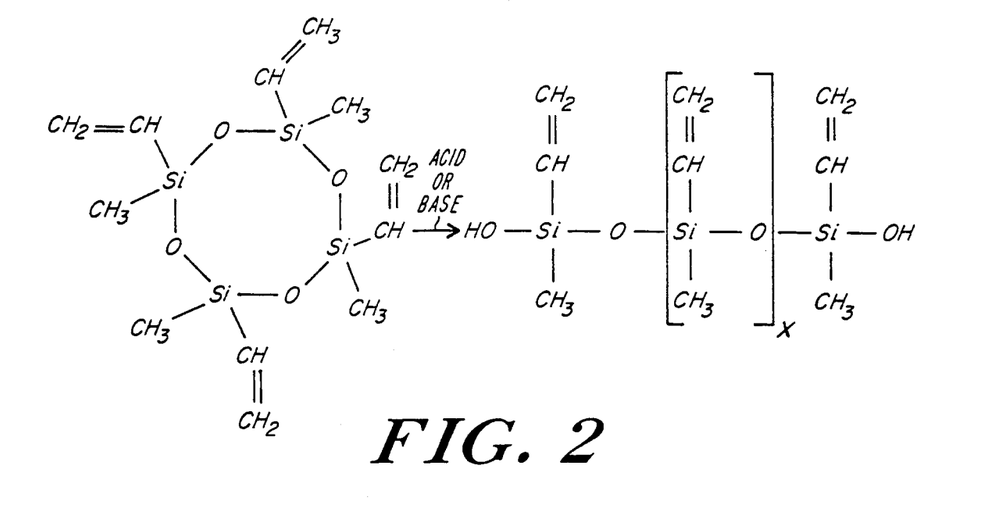
FIG. 2 shows the acid or base ring opening for synthesis of a siloxanediol.

The siloxanediol which is used for the preparation of sub-layer 12 is synthesized according to well-established procedures by acid or base catalysis from 1,3,5,7 tetravinyltetramethylcyclotetrasiloxane (see, e.g., Dean, J. W., "Silicone Adhesive Sealants and Abhesives," in Irving Skeisd, *Handbook of Adhesives*. N.Y. Van Nostrand, Reinhold (1990)). Referring to FIG. 2, 1,3,5,7 tetravinyltetramethylcyclotetrasiloxane undergoes ring-opening and condensation reactions to produce long polymers of siloxanediol. The molecular weight of the siloxanediol polymer may be controlled by the ratio of acid or base, respectively, to 1,3,5,7 tetravinyltetramethylcyclotetrasiloxane.

Figure 3:
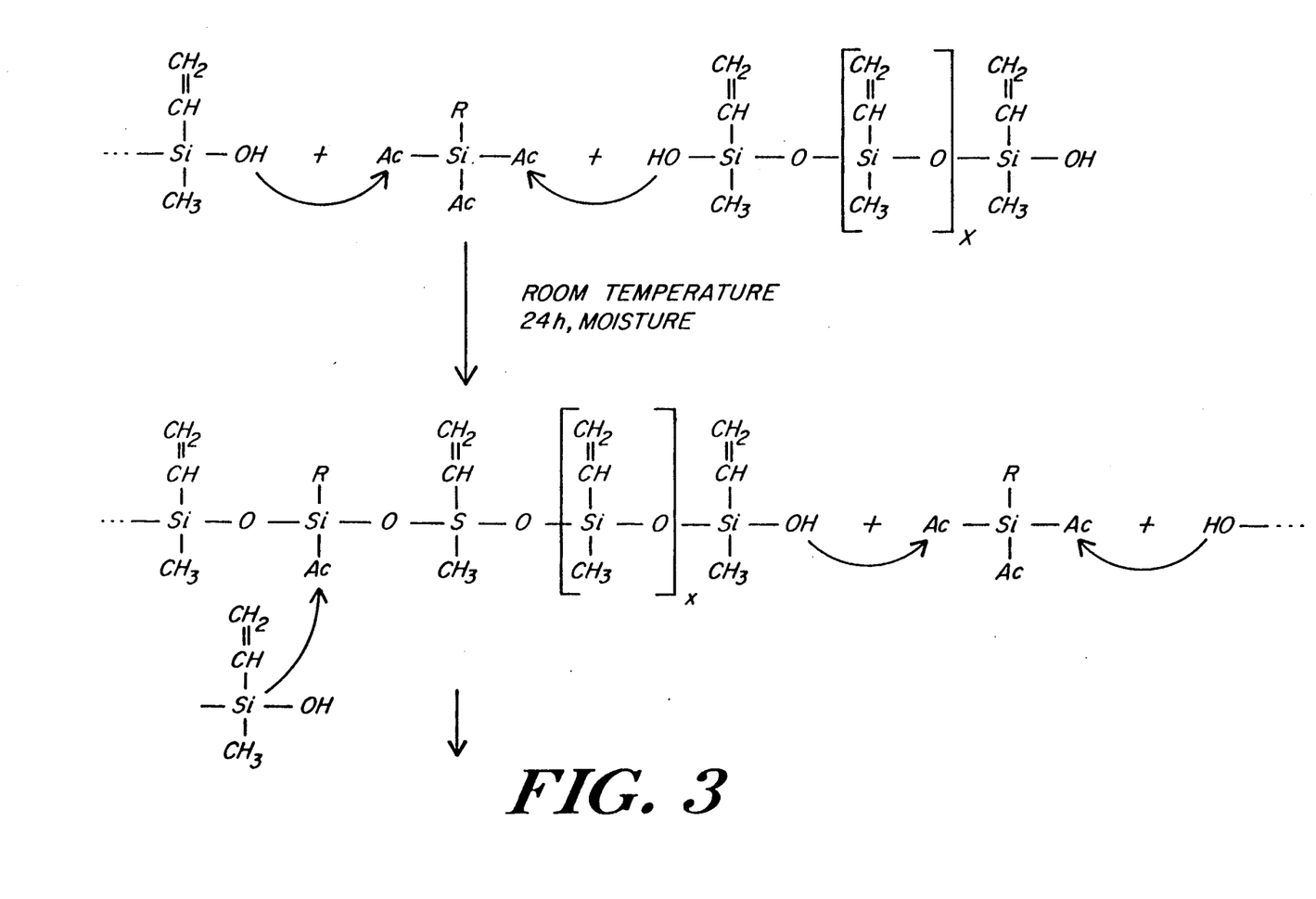
FIG. 3 shows crosslinking of siloxanediol polymers using a crosslinking agent at room temperature.

The siloxanediol polymer thus produced is dissolved in an appropriate ratio (e.g., 20:1, w/v) with a crosslinker, such as alkyltriacetoxysilane, in an anhydrous solvent, such as anhydrous ether (FIG. 3). The two components are then applied to the interior of an electrophoresis column (e.g., of fused silica) using the "static" method, in which the column is filled with the solution, closed at one end, and a vacuum applied at the other end. After evaporation of the solvent, the deposited film is exposed to moisture in the air for approximately 24 hours to induce crosslinking and covalent binding Alternatively, a single component system of, e.g., acyloxysiloxanediol may be used. This compound contains the siloxanediol polymer and a crosslinker in the same molecule. Exposure to moisture then continues the partially initiated crosslinking step.

Figure 4:
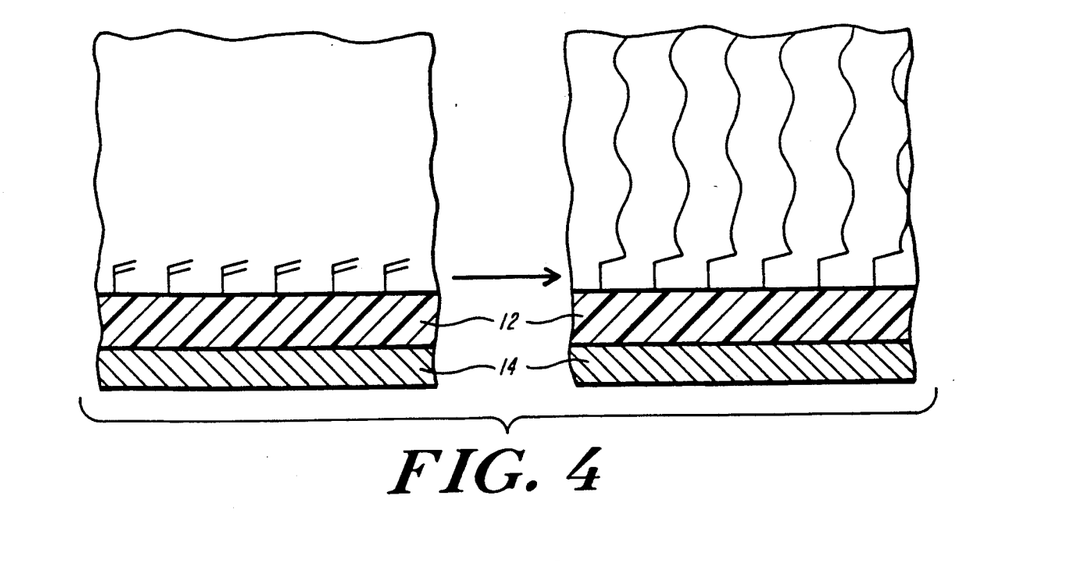
FIG. 4 shows grafting of acrylamide polymers to free vinyl groups of a siloxanediol sub-layer coating of the invention.

As only the diol end groups of the starting siloxanediol polymer are involved in the sub-layer crosslinking processes, the interior vinyl side chains of the sub-layer matrix are fully available for attachment of a top layer. To carry out such attachment, the column coated with crosslinked polymethylvinylsiloxanediol is filled with a solution of acrylamide, N,N,N',N'-tetramethylethylenediamine (TEMED), and ammonium persulfate. The acrylamide monomers polymerize and are grafted to the siloxanediol surface by reacting with the free vinyl groups as shown in FIG. 4. After approximately 12 hours, any non-grafted polyacrylamide is pushed out with a syringe.

To further stabilize the siloxanediol-polyacrylamide coating, the column is filled with an aqueous solution of formaldehyde adjusted to pH 10. As shown in Hunt et al., U.S. Pat. No. 3,214,420, the formaldehyde reacts with interior amide groups of the acrylamide to form methylolacrylamide, which densely crosslinks to form polymethylolacrylamide or top layer 16 (FIG. 1). After approximately 3 hours, the formaldehyde solution is pushed out with a syringe, and the column is ready for use. This two step crosslinking procedure is more easily controlled than standard one step methods of crosslinking polyacrylamide molecules using, e.g., bisacrylamide, or direct polymerization of methylacrylamide in the capillary. Any of a variety of other materials (e.g., shown in Example B) may be similarly attached to the crosslinked siloxanediol sub-layer. Additionally, the final top layer may be grafted to the sub-layer by adsorption instead of by covalent attachment. Possible components to be adsorbed among others are polyethyleneglycol (PEG), cellulose derivatives, dextran, or polyvinylalcohol.

The coating of the invention might also be used as an immobilized stationary phase in gas chromatography, HPLC and supercritical fluid chromatography. For this application, the siloxanediol layer (highly crosslinked and covalently attached to chromatographic support) would itself serve as an interactive surface. In HPLC the coating will provide a high pH stability. In principle, any hydrophobic or hydrophilic siloxanediol may be used to form the surface layer. For example, for reverse phase chromatography, polyalkylsiloxanediols could be used. By changing the type and the ratios of the alkyl groups, different chromatographic selectivities can be achieved. Specific selectivities can be introduced by binding special selectors (e.g., chiral selectors) to the siloxanediol layer.

Since highly crosslinked polymethylvinylsiloxanediol forms a smooth and firm film on almost any type of material, and since its double bonds allow the grafting of a wide variety of monomers and polymers with different properties, the coating of the invention might be further used in all fields where prevention of the adsorption of sample material is crucial. Those applications can be, e.g., the coating of glass plates, sample containers, stainless steel joints, pipette tips, electrospray mass spectroscopic tips, etc.

The chemical reactions for polymerization of the siloxanediol subunits are very easily carried out. Therefore, many additional modifications of the sub-layer are also within the scope of the invention. For example, siloxane polymers having any of a number of nucleophilic end groups (e.g., diamino or dithiol) can be formed by varying the reaction conditions for siloxanediol formation. These polymers can similarly be crosslinked with alkyltriacetoxysilane or any of a variety of appropriate crosslinkers (e.g., methyltrimethoxysilane, methyl tris(methylethylketoximino)silane, methyltris(cyclohexylamino)silane,methyltris(N-methylacetamido)silane, tetraethoxysilane, etc.). The crosslinked siloxanediol layer can, furthermore, contain a wide variety of groups for attachment of a second coating. Besides the vinyl reactivity centers described above, suitable reactive or interactive groups include, but are not limited to, alkyl, allyl, olefin, carbonyl or any non-nucleophilic agent. Additionally, the sites for attachment of an additional coating layer may have been provided by a mixture of polymers.

EXAMPLES

A) The polymethylvinylsiloxanediol can be synthesized by basic (Example I) and acidic catalysis (Example II), (FIG. 2).

Example I 25 ml 1,3,5,7-tetravinyltetramethylcyclotetrasiloxane and 0.1447 g powdered NaOH are heated to 140° C. After 3 h the viscous mixture is dissolved in ether and washed to neutrality with water. The ether solution is dried over $Na_2SO_4$ and the solvent evaporated. The slightly yellow polymethylvinylsiloxanediol has a viscosity of approximately 71 poise.

Example II 25 ml 1,3,5,7-tetravinyltetramethylcyclotetrasiloxane and 6.9 ml conc. $H_2SO_4$ are dissolved in 25 ml anhydrous ether. After 3 days stirring at room temperature the viscous mixture is washed to neutrality with water. The ether solution is dried over $Na_2SO_4$ and the solvent evaporated. The colorless polymethylvinylsiloxanediol has a viscosity of approximately 75 poise.

B) The highly crosslinked siloxanediol coating can be laid down by the static method as shown in Example III. After crosslinking and binding of the siloxanediol to the capillary surface at ambient temperature overnight (FIG. 3), either acrylamide (Example IV), vinyl-pyrrolidone (Example V) or N-acryloyltris(hydroxymethyl)aminoethane (NAT) (Example VI) is grafted to the polymer sub-layer (FIG. 3). The grafted polyacrylamide can further be converted with formaldehyde to polymethylolacrylamide which crosslinks automatically with itself (Example VII). Other monomers that can be used are, e.g., hydroxyethylmethacrylate (HEMA), vinyl acetate, N-(2-hydroxypropyl)methacrylamide, N-methacryloyltris(hydroxymethyl)-aminoethane, N-methylacrylamide, N,N-dimethylacrylamide, 2-acrylamido-2-methylpropanesulfonic acid, diallyldimethylammoniumchloride.

Example III 50 mg of the polymethylvinylsiloxanediol and 3 μl vinyltriacetoxysilane are dissolved in 4.6 ml anhydrous ether. The mixture is filled by syringe into a fused-silica column (i.d.=75 μm, l=70 cm). The column is closed at one end with a septum and a vacuum is applied at the other end. After complete evaporation of the solvent, the septum is removed and the column is exposed for 24 h to the moisture of the air. The film thickness is about 0.2 μm.

Example IV

A solution of 50 mg acrylamide in 1 ml water (5% monomer) is degassed for 30 min by bubbling through helium. 10 μl TEMED (10% in water w/v) and 10 μl APS (10% in water w/v) are added. The mixture is immediately pushed by syringe into the siloxanediol-coated column. After 12 h the polymerized but not grafted acrylamide is pushed out. The column is ready for use.

Example V

A solution of 400 mg vinyl-pyrrolidone in 1 ml water (40% monomer) is degassed for 30 min by bubbling through helium. The pH is adjusted to 10 with ammonium hydroxide (40%), and 7 μl $H_2O_2$ (30%) is added. The mixture is pushed by syringe into the siloxanediol coated column. After 30 min at 50° C. the column is rinsed with 50 μl water. The column is ready for use.

Example VI

A solution of 40 mg N-acryloyltris(hydroxymethyl)aminomethane (NAT) in 1 ml water (4% monomer) is degassed for 30 min by bubbling through helium. 3 μl TEMED (10% in water w/v) and 3 μl APS (10% in water w/v) are added. The mixture is immediately pushed by syringe into the siloxanediol-coated column. After 12 h the polymerized but not grafted NAT is pushed out. The column is ready for use.

Example VII

The polyacrylamide column of example IV is filled with a 37% solution of formaldehyde adjusted to pH 10 with NaOH. After 3 h the solution is rinsed with 50 μl water. The column is ready for use.

C) After formation of a sub-layer coating of polymethylvinylsiloxanediol, the vinyl double bonds can also be converted to epoxy groups (Example VIII) or diol groups (Example IX). By acidic catalysis, basic catalysis or heat treatment the epoxy groups can be reacted with nucleophilic polymers (e.g., polyethyleneglycol, polyethyleneimine or polyvinylalcohol) (Example VIII). In the presence of Ce(IV) the diol groups can be used to graft and polymerize vinyl monomers (acrylamide, vinyl acetate, vinyl pyrrolidone, etc.) to the siloxanediol core (Example IX). Furthermore, if charged groups are added to the sub-layer via the vinyl double bonds, they can serve to establish electroosmotic flow when an electric field is applied (Examples X, XI). These charged groups could also be screened by an appropriately chosen top layer, e.g., a polyether, so that moving solute ions would not be electrostatically adsorbed.

Example VIII

Columns were filled with a solution of 0.4 g chloroperbenzoic acid (50–60%) in 1 ml ether overnight. The next day the column was filled with a solution of 0.2 g PEG 600, 30 μl $BF_3$ in 1 ml dioxane. After 1 h at 100° C. the column was rinsed with methanol and then with water.

Example IX

Columns were filled with a solution of 0.5 ml water, 0.2 ml acetone, 24 mg (0.09 mmol) $OsO_4$ and 0.182 g (1.06 mM) N-methylmorpholine-N-oxide·$2H_2O$. After 24 h the columns were washed with water and filled with a solution of 0.5 g acrylamide, 10 ml water and 0.25 ml of 0.1M ceric ammonium sulfate in 1M nitric acid. After 12 h the columns were rinsed with water.

Example X 40 mg of the negatively charged 2 acrylamido-2-methylpropanesulfonic acid in 1 ml water are degased for 30 min by bubbling through helium. 5 µl TEMED (10% w/v) and 5 µl APS (10% w/v) are added. The silanediol coated columns are immediately filled with the solution. After 12 h the solution is pushed out and the columns are ready for use. The negatively charged coating creates a strong eof to the cathode.

Example XI 320 mg of the positively charged diallyldimethylammonium chloride in 1 ml water are degased for 30 min by bubbling through helium. 20 µl TEMED (10% w/v) and 20 µl APS (10% w/v) are added. The silanediol coated columns are immediately filled with the solution. After 12 h the solution is pushed out and the columns are ready for use. The positively charged coating creates a strong eof to the anode.

D) The bilayer coating of the invention has been used successfully in open tube CZE separations of proteins (Examples XII, XIII), in SDS gel separations of proteins (Example XIV), in gel separations of DNA (Example XV), and in DNA sequencing separations (Example XVI). But other applications are not excluded.

Figure 5:
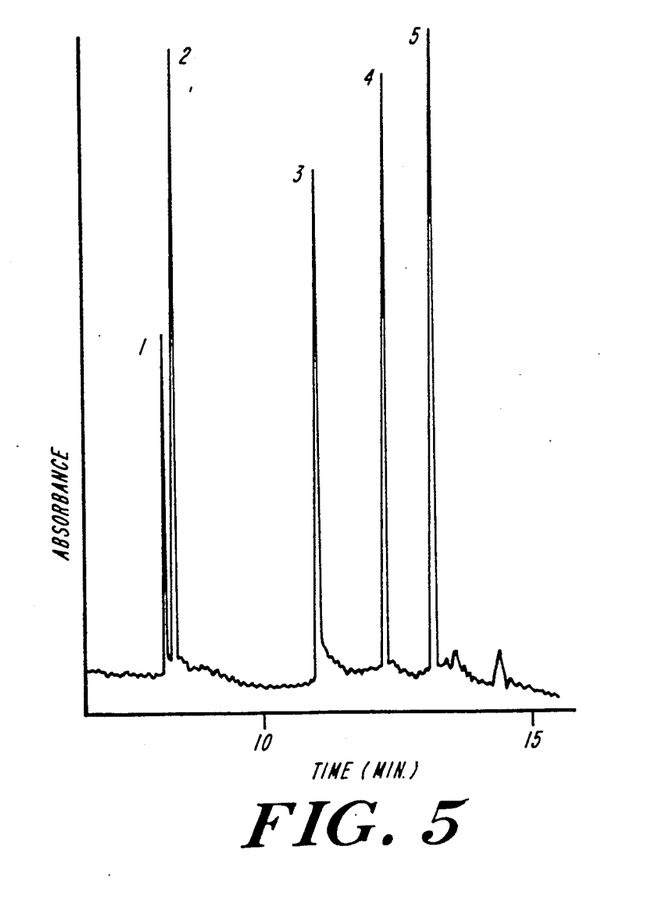
FIG. 5 shows open tube capillary zone electrophoresis of basic proteins at pH 4.4, using a microcapillary column of the invention.

Example XII (FIG. 5)

Sample: (1) lysozyme, (2) cytochrome c, (3) RNase, (4) myoglobin, (5) trypsinogen. Coating: Example IV. Conditions: total length L=56 cm, length from the injection end to the detector l=28 cm, i.d.=75 µm; detection UV 214 nm, 15 kV, 7 µA; buffer: 20 mM ϵ-amino-caproic acid (pH 4.4).

Figure 6:
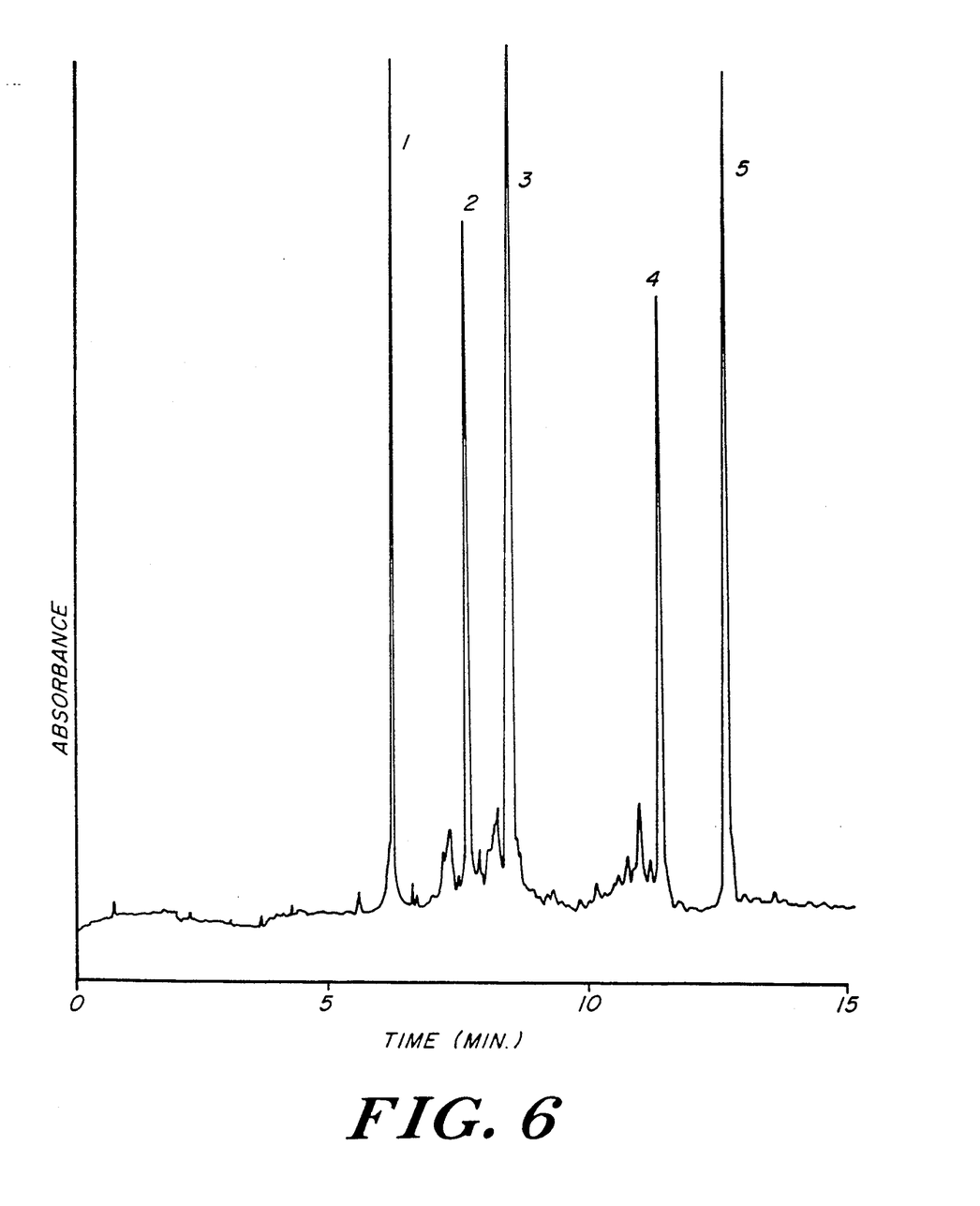
FIG. 6 shows open tube capillary zone electrophoresis of acidic proteins at pH 8.8, using a microcapillary column of the invention.

Example XIII (FIG. 6)

Sample: (1) glucose-6-phosphatedehydrogenase, (2) trypsin inhibitor, (3) β-lactoglobulin A, (4) L-asparaginase, (5) αlactalbumin. Coating: Example IV. Conditions: as in Example XII except the buffer: 20 mM TAPS (pH 8.8).

Figure 7:
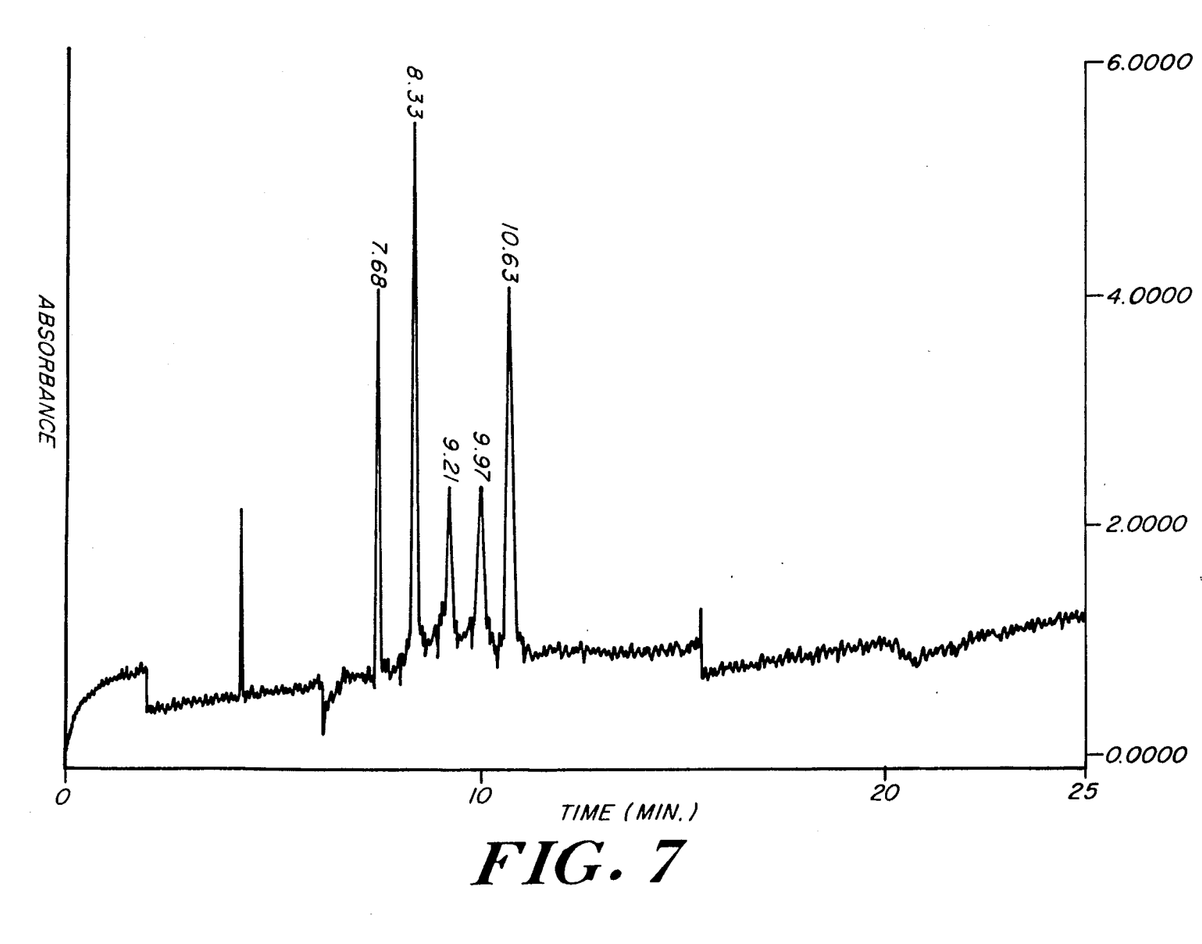
FIG. 7 shows SDS polymer network separation of proteins using a microcapillary column of the invention.

Example XIV (FIG. 7)

Sample: reduced protein-SDS complexes, (1) myoglobin, (2) carbonic anhydrase, (3) ovalbumin, (4) bovine serum albumin, (5) phosphorylase B. Coating: Example V. Conditions: total length L=25 cm, length from the injection end to the detector l=18 cm, i.d.=75 µm; const. current 30 µA for 25 min, 6.5 kV; buffer and polymer network 10% (w/v) dextran (MW 2,000,000) dissolved on 70 mM amino-methyl-propanediol, 0.6% SDS/TES (pH 8.1).

Figure 8:
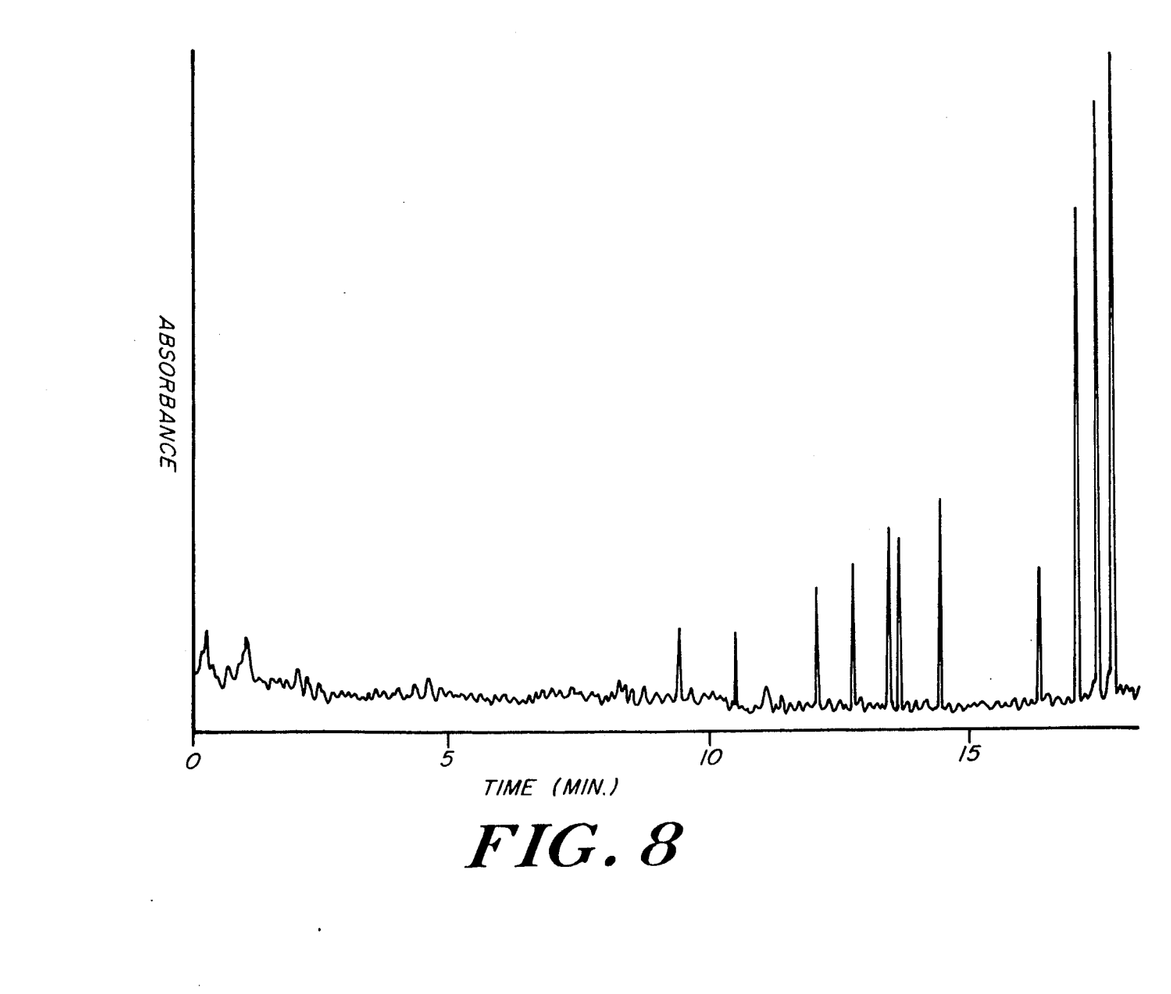
FIG. 8 shows polymer network separations of DNA using a microcapillary column of the invention.

Example XV (FIG. 8)

Sample: DNA ΦX174-HaeIII. Coating: Example IV. Conditions: total length L=56 cm, length from the injection end to the detector l=30 cm, i.d.=75 µm; detection: UV 260 nm; 300 V/cm, 13 µA; buffer and polymer network 3% polyacrylamide.

Figure 9A:
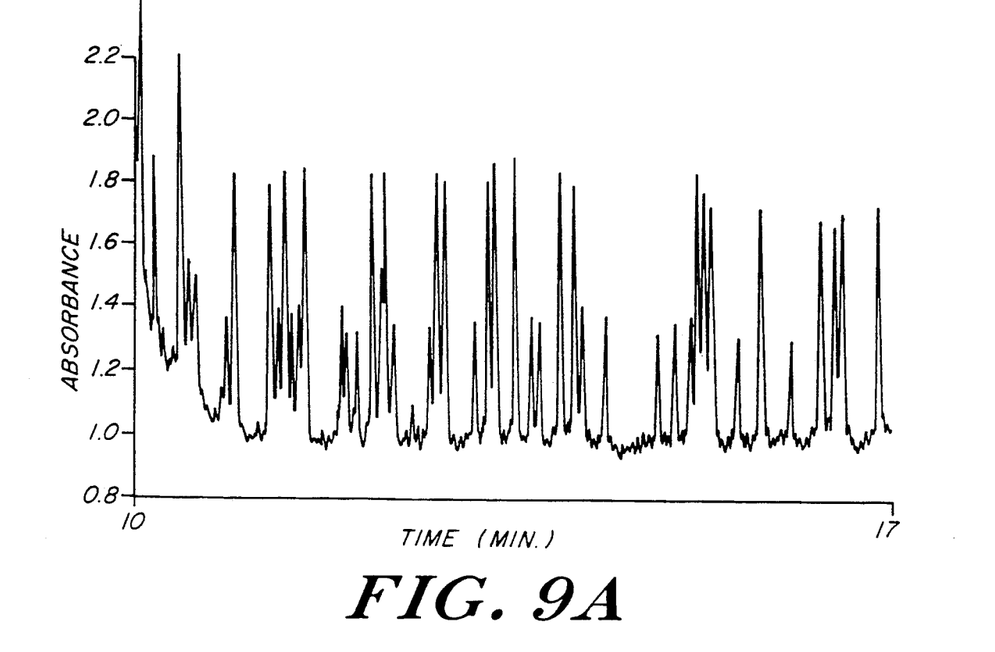
FIGS. 9A and 9B shows polymer network separations of DNA reaction products using a microcapillary column of the invention.
Figure 9B:
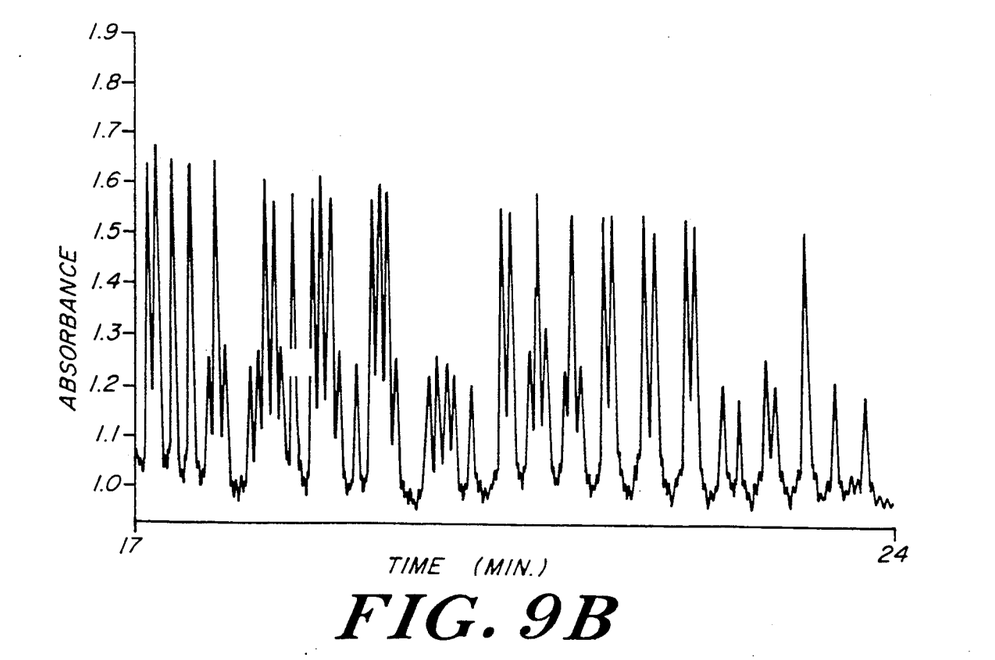

Example XVI (FIGS. 9A and 9B)

Sample: sequencing of M13mp18 single stranded phage DNA using FAM—labeled M13 (−21) primers (ABI), (A>G). Coating Example IV. Total length L=33 cm, length from injection end to the detector l=18 cm, i.d.=75 µm. A section of the electropherogram is shown. Separation matrix: 6% T acrylamide polymerized with 0.5 µl of 100% TEMED and 1.0 µl of 10% APS. Field: 250 V/cm. Separation temperature: 24° C. Electro-kinetic injection: 7 sec. Gel buffer: 1×TBE+30% (v/v) formamide+3.5M urea.

E) In other embodiments a top layer can be laid down by adsorptive coating.

Example XVII

Siloxane coated columns are filled with a 1% water solution of cellulose (high viscosity). After 12 h, the solution is pushed out, and the column is ready for use. Instead of cellulose, 0.5% PVA 124 000 water solution can be used in the same way.

Other embodiments of the invention will be apparent to those skilled in the art from a consideration of this specification or practice of the invention as disclosed herein. It is intended that the specification and examples be considered as exemplary only, with the true scope and spirit of the invention being indicated by the following claims.

What is claimed is:

1. A microcapillary column for high precision and high performance electrophoresis, comprising:
   a microcapillary having an interior cavity and a wall with an inner surface;
   a sub-layer of a siloxanediol polymeric coating material, highly crosslinked with a crosslinking agent and attached covalently or non-covalently to said inner surface of said wall; and
   a top layer of a coating material attached covalently or non-covalently to said sub-layer coating material.

2. The microcapillary column of claim 1 wherein said microcapillary is made of fused silica.

3. The microcapillary column of claim 1 wherein said top layer of coating material is crosslinked.

4. The microcapillary column of claim 1 wherein said sub-layer coating material is polymethylvinylsiloxanediol.

5. The microcapillary column of claim 1 wherein said top layer of coating material comprises uncrosslinked polyacrylamide.

6. The microcapillary column of claim 1 wherein said top layer of coating material comprises crosslinked polyacrylamide.

7. The microcapillary column of claim 1 wherein said top layer of coating material is polymethylolacrylamide.

8. A microcapillary column for high precision and high performance electrophoresis, comprising:
   a fused silica microcapillary having an interior cavity and a wall with an inner surface;
   a sub-layer of coating material covalently bonded to said inner surface of said wall, wherein said coating material is highly crosslinked polymethylvinylsiloxanediol; and
   a top layer of coating material covalently bonded to said sub-layer of coating material, said top layer comprising polyacrylamide.

9. The microcapillary column of claim 8 wherein said polyacrylamide is crosslinked polyacrylamide.

10. The microcapillary column of claim 8 wherein said polyacrylamide is polymethylolacrylamide.

* * * * *

UNITED STATES PATENT AND TRADEMARK OFFICE
CERTIFICATE OF CORRECTION

PATENT NO. : 5,322,608

DATED : June 21, 1994

INVENTOR(S) : Barry L. Karger, et al.

It is certified that error appears in the above-indentified patent and that said Letters Patent is hereby corrected as shown below:

On the title page, item [54] and Col. 1, line 1,
In the title, "SILOXANDEDIOL" should read --SILOXANEDIOL--.

In the Abstract, line 19, "groups, e.q." should read
--groups, e.g.--.

In Fig. 2, the top bonded chain should read:

Column 3, line 33, "TEFLON$_{TM}$" should read --TEFLON$^{TM}$--.

Signed and Sealed this

Twenty-first Day of February, 1995

Attest:

BRUCE LEHMAN

*Attesting Officer*     *Commissioner of Patents and Trademarks*